United States Patent
Ha et al.

(10) Patent No.: US 10,405,900 B2
(45) Date of Patent: Sep. 10, 2019

(54) APPARATUS FOR FIXING CERVICAL SPINE

(71) Applicant: SOLCO BIOMEDICAL CO., LTD., Pyeongtaek-si (KR)

(72) Inventors: Myung Heon Ha, Osan-si (KR); Il Kim, Seoul (KR)

(73) Assignee: SOLCO BIOMEDICAL CO., LTD., Pyeongtaek-si (KR)

( * ) Notice: Subject to any disclaimer, the term of this patent is extended or adjusted under 35 U.S.C. 154(b) by 77 days.

(21) Appl. No.: 15/716,774

(22) Filed: Sep. 27, 2017

(65) Prior Publication Data
US 2019/0046245 A1 Feb. 14, 2019

(30) Foreign Application Priority Data
Aug. 8, 2017 (KR) .................. 10-2017-0100466

(51) Int. Cl.
*A61B 17/80* (2006.01)
*A61B 17/70* (2006.01)

(52) U.S. Cl.
CPC ...... *A61B 17/8042* (2013.01); *A61B 17/7059* (2013.01)

(58) Field of Classification Search
CPC .. A61B 17/80; A61B 17/8033; A61B 17/8042
USPC ........................ 606/289, 295, 296
See application file for complete search history.

(56) References Cited

U.S. PATENT DOCUMENTS

| | | | | |
|---|---|---|---|---|
| 5,951,558 A * | 9/1999 | Fiz | ..... | A61B 17/8042 606/291 |
| 6,139,550 A * | 10/2000 | Michelson | ..... | A61B 17/1604 606/287 |
| 6,152,927 A * | 11/2000 | Farris | ..... | A61B 17/7059 606/287 |
| 6,306,139 B1 * | 10/2001 | Fuentes | ..... | A61B 17/1728 606/295 |
| 6,398,783 B1 * | 6/2002 | Michelson | ..... | A61B 17/1604 606/246 |
| 6,428,542 B1 * | 8/2002 | Michelson | ..... | A61B 17/1604 606/246 |
| 6,652,525 B1 * | 11/2003 | Assaker | ..... | A61B 17/7059 606/296 |
| 7,041,105 B2 * | 5/2006 | Michelson | ..... | A61B 17/7059 606/247 |

(Continued)

FOREIGN PATENT DOCUMENTS

| JP | 2008100101 A | 5/2008 |
|---|---|---|
| JP | 2008119491 A | 5/2008 |
| KR | 10-0552117 B1 | 2/2006 |

*Primary Examiner* — Eric S Gibson
(74) *Attorney, Agent, or Firm* — Dilworth IP, LLC (57) ABSTRACT

Disclosed herein is an apparatus for fixing a cervical spine. The apparatus for fixing a cervical spine includes a plate in which a plurality of screw insertion holes is formed, bone screws inserted into the screw insertion holes and screwed onto a bone fragment through rotation, and a locking part rotatably coupled to the plate to open or close a top of the screw insertion hole. A stepped part of a specific depth is formed on top of the plate. The stepped part includes a rotation area in which the locking part is capable of rotating. A locking part insertion hole is formed in the rotation area so that the locking part is inserted into locking part insertion hole.

6 Claims, 5 Drawing Sheets

(56) References Cited

U.S. PATENT DOCUMENTS

| | | | | |
|---|---|---|---|---|
| 7,044,952 B2* | 5/2006 | Michelson | A61B 17/7059 | 606/282 |
| 7,306,605 B2* | 12/2007 | Ross | A61B 17/7059 | 606/70 |
| 7,674,279 B2* | 3/2010 | Johnson | A61B 17/8042 | 606/295 |
| 7,727,266 B2* | 6/2010 | Lindemann | A61B 17/7059 | 606/289 |
| 7,875,062 B2* | 1/2011 | Lindemann | A61B 17/8042 | 606/280 |
| 8,262,705 B2* | 9/2012 | Bray | A61B 17/7059 | 606/280 |
| 8,454,667 B2* | 6/2013 | Humphreys | A61B 17/8042 | 606/286 |
| 8,486,115 B2* | 7/2013 | Fisher | A61B 17/8042 | 606/286 |
| 8,652,182 B1* | 2/2014 | Walker | A61B 17/7059 | 606/295 |
| 8,906,077 B2* | 12/2014 | Bush, Jr. | A61B 17/8042 | 606/296 |
| 8,932,335 B2* | 1/2015 | Humphreys | A61B 17/7059 | 606/294 |
| 9,381,093 B1* | 7/2016 | Morris | A61B 17/7059 | |
| 2003/0187440 A1* | 10/2003 | Richelsoph | A61B 17/7059 | 606/287 |
| 2004/0220571 A1* | 11/2004 | Assaker | A61B 17/7059 | 606/296 |
| 2004/0236335 A1* | 11/2004 | Michelson | A61B 17/1604 | 623/17.11 |
| 2005/0059971 A1* | 3/2005 | Michelson | A61B 17/1604 | 623/17.11 |
| 2005/0075633 A1* | 4/2005 | Ross | A61B 17/7059 | 606/280 |
| 2005/0187553 A1* | 8/2005 | Grabowski | A61B 17/7059 | 606/295 |
| 2005/0283152 A1* | 12/2005 | Lindemann | A61B 17/7059 | 606/281 |
| 2006/0247639 A1* | 11/2006 | Anderson | A61B 17/8042 | 606/281 |
| 2011/0022097 A1* | 1/2011 | Walker | A61B 17/7059 | 606/296 |
| 2015/0066096 A1* | 3/2015 | Bush, Jr. | A61B 17/7059 | 606/295 |
| 2016/0022335 A1* | 1/2016 | Humphreys | A61B 17/8042 | 606/279 |
| 2016/0095637 A1 | 4/2016 | Elsbury et al. | | |
| 2016/0135850 A1* | 5/2016 | Kim | A61B 17/7059 | 606/296 |
| 2017/0065311 A1 | 3/2017 | George et al. | | |

* cited by examiner

APPARATUS FOR FIXING CERVICAL SPINE

FIELD OF THE INVENTION

The present invention relates to an apparatus for fixing a cervical spine, which is used when an operation for fixing the front of a cervical spine is performed in orthopedics or neurosurgery and, more particularly, to an apparatus for fixing a cervical spine, which can easily fix a bone screw inserted into the screw insertion hole of a plate using a rotatable locking part.

BACKGROUND OF THE INVENTION

In general, in orthopedics or neurosurgery, when a cervical spine intervertebral disc disease, a cervical spine disk, cervicospinal myelosis or a cervical spine fracture is treated, cervical spines must be fixed to not move. To this end, an apparatus for fixing a cervical spine, including a plate of a sheet form and a screw for fixing the plate to a cervical spine, is used.

A surgical procedure using the apparatus for fixing a cervical spine is performed in such a way as to cut a lesion from the neck portion of a patient, expose a cervical spine, to perform a surgical procedure matter, such as a cage for the cervical spine, on the cervical spondylosis lesion, to locate the plate at the top and bottom of the lesion, and then to fix a corresponding plate by a screw.

Accordingly, the surgical procedure matter, such as the cage that has operated on the cervical spine, is fixed by fixation power of the screw and bearing power of the plate of the apparatus for fixing a cervical spine.

However, a phenomenon in which the screw becomes loose from the plate of the apparatus for fixing a cervical spine due to the activities of a patient after a surgical procedure and then retreats from the plate may be generated. From among conventional technologies for preventing such a phenomenon, Korean Patent No. 10-0552117 (CERVICAL SPINE FIXATOR AND DRIVER) and U.S. Patent Application Publication No. US 2016-0095637 (LOCKING MECHANISM FOR A CERVICAL FIXATION PLATE) have been known.

The contents of the prior arts are described below. In Korean Patent No. 10-0552117, the deviation of a screw is prevented by inserting the screw into an open part formed in a plate and seating a fixing member in a reset part. In U.S. Patent Application Publication No. US 2016-0095637, the deviation of a bone screw is prevented by inserting the bone screw into a bone screw opening formed in a plate body and coupling a locking element to a rocking post.

However, Korean Patent No. 10-0552117 has a problem in that it is inconvenient to perform rivet coupling on the plate in order to seat the fixing member. U.S. Patent Application Publication No. US 2016-0095637 has problems in that the locking element protruded outside the plate body may be caught in another thing and damaged due to a movement of a patient and the rocking post must be separated processed in the plate body.

PRIOR ART DOCUMENT

Patent Document (Patent Document 1) Korean Patent No. 10-0552117
(Patent Document 2) U.S. Patent Application Publication No. US 2016-0095637

SUMMARY OF THE INVENTION

Accordingly, the present invention has been made keeping in mind the above problems occurring in the prior art, and an object of the present invention is to provide an apparatus for fixing a cervical spine, which can prevent a locking part from deviating from a plate or from being caught and damaged despite the activities of a patient because the locking part for preventing the drawing of a bone screw is seated in a stepped part and allows an operator to simply prevent the drawing of the bone screw by rotating the locking part.

An embodiment of the present invention provides an apparatus for fixing a cervical spine, including a plate in which a plurality of screw insertion holes is formed, bone screws inserted into the screw insertion holes and screwed onto a bone fragment through rotation, and a locking part rotatably coupled to the plate to open or close a top of the screw insertion hole. A stepped part of a specific depth is formed on top of the plate. The stepped part includes a rotation area in which the locking part is capable of rotating. A locking part insertion hole is formed in the rotation area so that the locking part is inserted into locking part insertion hole.

The locking part includes a vertical part inserted into the locking part insertion hole, a horizontal part integrally coupled to the vertical part and coming into surface contact with the rotation area, and a plurality of fixing wings formed in the horizontal part and simultaneously opening or shutting the tops of two screw insertion holes adjacent to the rotation area.

An angle between the plurality of fixing wings is 120°.

A central area to guide the rotation of the locking part is provided between a plurality of the rotation areas provided in the stepped part, the fixing wing located in the rotation area shuts the top of the screw insertion hole, and the fixing wing located in the central area opens the top of the screw insertion hole.

A molding head part is formed at one end of the vertical part in order to prevent the locking part from being drawn after the locking part is inserted into the locking part insertion hole.

A rotation hole is formed in the horizontal part so that the rotation hole is coupled to a rotation tool and rotates the locking part.

| <Description of reference numerals> | |
|---|---|
| 1: apparatus for fixing a cervical spine | 10: plate |
| 12a, 12b, 12c: screw insertion hole | |
| 14a, 14b, 14c: locking part insertion hole | |
| 16: first stepped part | 17: second stepped part |
| 18: vision hole | 19: vision hole |
| 20: bone screw | 22: head part |
| 24: shaft | 26: clamping device hole |
| 30: locking part | 32: vertical part |
| 33: molding head part | 34: horizontal part |
| 35a, 35b: fixing wing | 36: rotation hole |

DETAILED DESCRIPTION OF THE INVENTION

An embodiment of an apparatus for fixing a cervical spine according to the present invention described in detail with reference to the accompanying drawings. Terms or words used herein should not be construed as having common or dictionary meanings, but should be construed as having meanings and concepts that comply with the technological spirit of the present invention on the basis of the principle that the inventor may appropriately define the concepts of the terms in order to best describe his or her invention.

Figure 1:
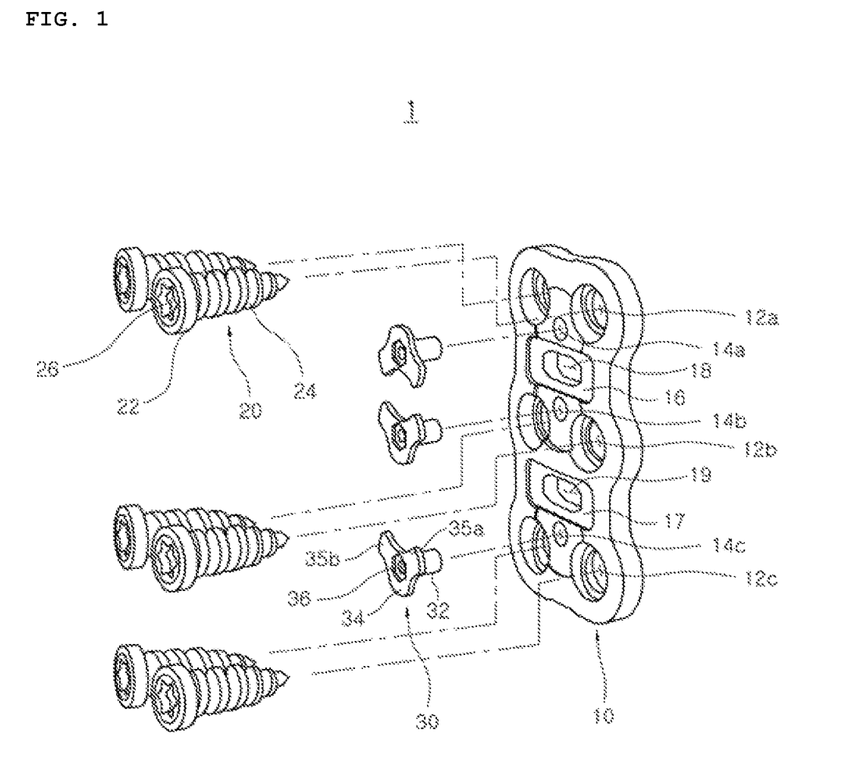
FIG. 1 is an exploded perspective view of an apparatus for fixing a cervical spine according to an embodiment of the present invention.

Referring to FIG. 1, the apparatus 1 for fixing a cervical spine according to an embodiment of the present invention can easily fix a bone screw 20 inserted into a plate 10 at a desired angle, and includes the plate 10, the bone screw 20 and a locking part 30.

The plate 10 is fixing means used to fix a bone fragment generated in the body of a person or an animal and has an approximately rectangular parallelepiped panel shape. The plate is outward protruded along the curved surface of a portion to which the bone screw 20 is coupled. The shape of the plate 10 may be changed depending on the shape of a bone fragment.

The plate 10 may be made of a rigid metal material, such as titanium, or a polymer material, such as polyether ether ketone, but the shape and material of the plate 10 are not limited to the aforementioned shape and materials. A rigid material for fixing a bone fragment which does not an adverse reaction when it is inserted into the human body may be used. The plate 10 includes screw insertion holes 12a, 12b and 12c and stepped parts 16 and 17.

The bone screws 20 to be described later are inserted into the screw insertion holes 12a, 12b and 12c. An insertion path that penetrates from the top of the plate 10 to the bottom is formed. The screw insertion holes 12a, 12b and 12c are formed to be symmetrical to an axis in the length direction of the plate 10. Three pairs of the screw insertion holes 12a, 12b and 12c have been shown in FIG. 1, but the screw insertion holes 12a, 12b and 12c that are more than three pairs or less than three pairs may be configured in the plate 10.

Central axes formed in the screw insertion holes 12a, 12b and 12c may be perpendicular to the top and bottom of the plate 10, but may be configured at a specific angle. For example, as shown in FIG. 1, the central axes of a pair of the screw insertion holes 12a that belong to the three pairs of screw insertion holes 12a, 12b and 12c and that are located on the upper side may be configured to become close each other. The central axes of a pair of the screw insertion holes 12b that belong to the three pairs of screw insertion holes 12a, 12b and 12c and that are located in the middle may be configured in the direction perpendicular to the top and bottom of the plate 10. The central axes of a pair of the screw insertion holes 12c that belong to the three pairs of screw insertion holes 12a, 12b and 12c and that are located on the lower side may be configured to become distant from each other. The angles of the central axes are formed by processing the screw insertion holes 12a, 12b and 12c in the direction of the central axis depending on the shape of a bone fragment to be fixed.

The inner surface of the screw insertion hole 12a, 12b, 12c may be formed to have a tapered surface or may be formed as a counter bore position having a latching jaw through the upper hole and the lower hole so that after the bone screw 20 is inserted into a cervical spine, the plate 10 is not drawn to a direction opposite the direction in which the bone screw 20 is inserted. In an embodiment of the present invention, the inner surface of the screw insertion hole 12a, 12b, 12c has been illustrated as having a tapered surface.

The stepped parts 16 are 17 are areas in which steps have been formed from the top of the plate 10 to the bottom thereof in order to seat the locking parts 30. The stepped part may include a rotation area and a central area. Referring to FIG. 1, the stepped parts 16 and 17 include a first stepped part 16 and a second stepped part 17. The first stepped part 16 includes a pair of rotation areas symmetrical to each other on the basis of the central area. The second stepped part 17 includes a central area and a rotation area.

The rotation area is provided between the pairs of screw insertion holes 12a, 12b and 12c and has a rotation path having specific curvature so that the locking part 30 can rotate. Locking part insertion holes 14a, 14b and 14c that penetrate from the top of the plate 10 to the bottom thereof are configured in the rotation areas. Accordingly, the depth of the screw insertion holes 12a, 12b and 12c and the depth of the locking part insertion holes 14a, 14b and 14c have a difference corresponding to the step.

The central area is connected to the rotation area and provided between a pair of the screw insertion holes 12a and 12b and between a pair of the screw insertion holes 12b and 12c. The central areas are spaced apart from each other in the length direction of the plate 10 so that it does not hinder rotation between a plurality of the locking parts 30 located in the rotation areas. Vision holes 18 and 19 formed to have a form that penetrates the plate 10 and to allow the procedure state of the apparatus 1 for fixing a cervical spine to be easily checked are configured in the central area.

Referring to FIG. 1, the stepped parts 16 and 17 include the first stepped part 16 and the second stepped part 17. The first stepped part 16 has a pair of rotation areas symmetrical to each other on the basis of the central area. The second stepped part 17 has the central area and the rotation area. However, if four pairs of the screw insertion holes are configured as described above, the second stepped part 17 may have a central area and a rotation area, such as those of the first stepped part 16.

The bone screw 20 may include a head part 22 and a shaft 24 in order to be inserted into the screw insertion hole 12a, 12b, 12c of the plate 10.

A clamping device hole 26 into which a clamping device (not shown) is inserted may be formed at the top of the head part 22 so that the bone screw 20 is coupled to a cervical spine (not shown). In FIG. 1, the clamping device hole 26 has been formed to have a star shape, but may have a different shape for coupling the clamping device hole 26 and the clamping device (not shown).

The outer surface of the head part 22 may have a tapered surface in such a way as to correspond to the inner surface of the screw insertion hole 12a, 12b, 12c. That is, the inner surface of the screw insertion hole 12a, 12b, 12c and the outer surface of the bone screw 20 can be compressed and brought in contact with each other with inclination due to the shape of the inner surface of the head part 22. Accordingly, after the bone screw 20 is inserted into the cervical spine, the drawing of the plate 10 is prevented.

The shaft 24 has one end integrally coupled to the head part 22 and inclined toward the other end to have a screw form. A screw thread formed in one direction to be easily coupled to the cervical spine is configured in the outer surface of the shaft 24.

As described above, the axis in which the screw insertion hole 12a, 12b, 12c is inserted can be processed to be inclined at a specific angle. Accordingly, the bone screw 20 inserted into the inclined screw insertion hole 12a, 12b, 12c moves with inclination in the direction of the central axis of the screw insertion hole 12a, 12b, 12c and screw-coupled to the cervical spine. Accordingly, a task for fixing bone fragments of various forms can be performed depending on the angle of the central axis of the screw insertion hole 12a, 12b, 12c.

The diameter of the top of the bone screw 20 may be smaller than that of the top of the screw insertion hole 12a, 12b, 12c. Accordingly, the bone screw 20 is inserted into the screw insertion hole 12a, 12b, 12c, moved and stopped at a portion where the diameter of the top of the bone screw 20 is the same as the diameter of the top of the bone screw 20 in the inner surface of the screw insertion hole 12a, 12b, 12c. Accordingly, the top of the bone screw 20 is not protruded outside the top of the screw insertion hole 12a, 12b, 12c.

The locking part 30 is inserted into the plate 10 and is for fixing the bone screw 20 in order to prevent the drawing of the bone screw 20 depending on a rotation angle. The locking part includes a vertical part 32 and a horizontal part 34.

Figure 2:
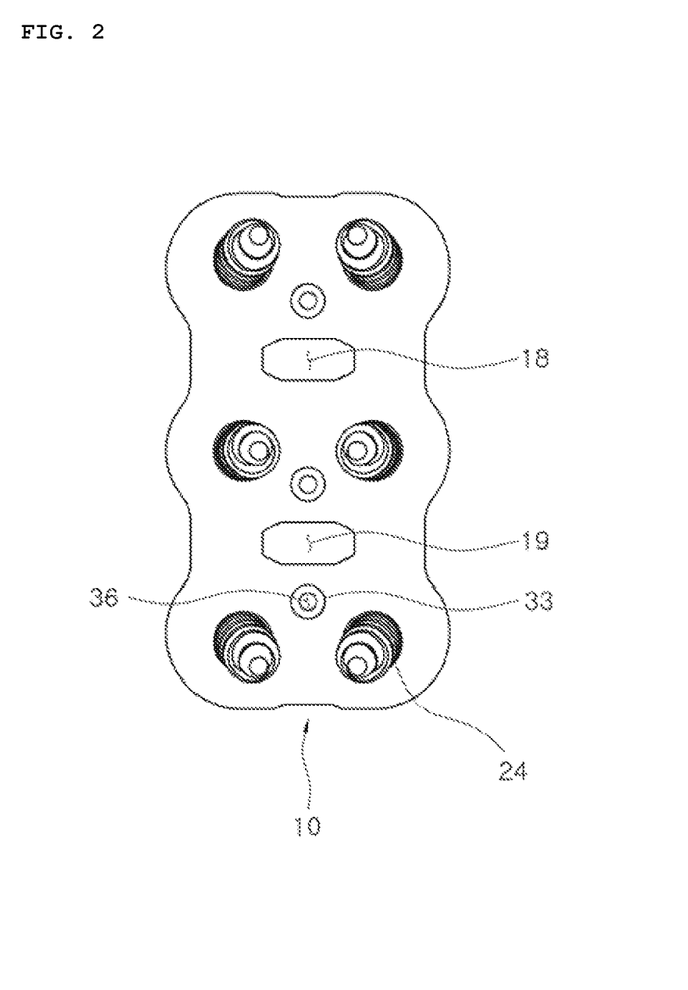
FIG. 2 is a rear view of the apparatus for fixing a cervical spine according to an embodiment of the present invention.

Referring to FIGS. 1 and 2, the vertical part 32 has a cylindrical hollow shape so that it is inserted into the locking part insertion hole 14a, 14b, 14c provided in the plate 10 and rotated therein. In the state in which the locking part 30 has been inserted into the locking part insertion hole 14a, 14b, 14c, one end of the vertical part 32 is coupled to the horizontal part 34 and integrated therewith, thereby preventing drawing in the downward direction of the locking part 30. Furthermore, the other end of the vertical part 32 forms a molding head part 33a to prevent drawing in the upward direction of the locking part 30.

A rotation hole 36 is provided in the horizontal part 34 to communicate with the hollow of the vertical part 32. When a driver (not shown) is inserted into the rotation hole 36 and rotated, the integrally formed vertical part 32 and horizontal part 34 can rotate in the rotation area of the stepped part 16, 17 on the basis of the central axis of the rotation hole 36. In the state in which the horizontal part 34 has been inserted into the locking part insertion hole 14a, 14b, 14c, the top of the horizontal part 34 is almost identical with the top of the plate 10 due to the depth of the depth of the rotation area. Accordingly, a phenomenon in which the locking part 30 is caught in the outside due to a movement of a patient can be prevented.

Fixing wings 35a and 35b are provided on both sides of the horizontal part 34 so that the top of the screw insertion hole 12a, 12b, 12c is closed and rotation in the rotation area of the stepped part 16, 17 is facilitated depending on a rotation angle. FIG. 1 shows the two fixing wings 35a and 35b having an angle of 120° between extension lines that connect the central axis of the rotation hole 36 and the fixing wings 35a and 35b (hereinafter referred to as a "wing angle"). However, the wing angle may be set so that an angle between extension lines that connects the central axes of the screw insertion holes 12a, 12b and 12c adjacent to the locking part insertion holes 14a, 14b and 14c in the central axes of the locking part insertion holes 14a, 14b and 14c (hereinafter referred to as a "closed angle"). For example, if the closed angle is 180°, the wing angle may be set to 180°. Furthermore, the number of fixing wings 35a and 35b is not limited to 2 and may be two or more if the top of the screw insertion hole 12a, 12b, 12c can be closed by the locking part 30. The size and shape of the fixing wings 35a and 35b may be configured in various manners.

The operation of the locking part 30 is described in detail with reference to FIGS. 3 to 5.

Figure 3:
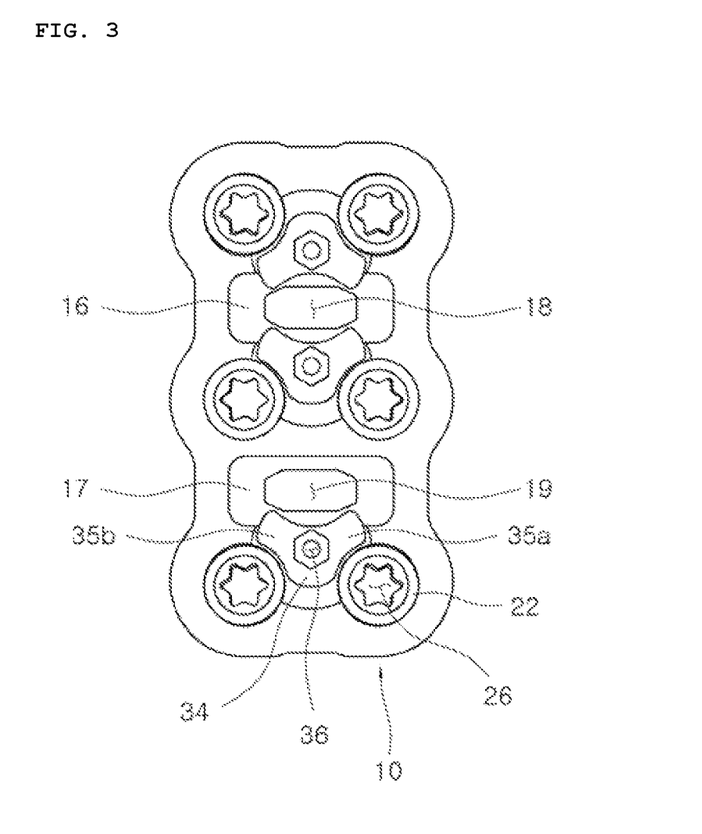
FIG. 3 is a plan view showing the state in which the fixing wing of the apparatus for fixing a cervical spine is located in a central area according to an embodiment of the present invention.

Referring to FIG. 3, the bone screws 20 have been inserted into the screw insertion holes 12a, 12b and 12c of the plate 10, and the locking parts 30 have been inserted into the locking part insertion holes 14a, 14b and 14c. The fixing wings 35a and 35b of the locking part 30 inserted into the locking part insertion hole 14a over the first stepped part 16 and the fixing wings 35a and 35b of the locking part 30 inserted into the locking part insertion hole 14b under the first stepped part 16 face each other on the basis of the central area of the first stepped part 16. The fixing wings 35a and 35b of the locking part 30 inserted into the locking part insertion hole 14c of the second stepped part 17 are set toward the central area of the second stepped part 17. If such setting is performed, the fixing wings 35a and 35b open the tops of the screw insertion holes 12a, 12b and 12c. Accordingly, when the fixing wings 35a and 35b face toward the central area of the stepped part 30, the fixing wings 35a and 35b do not fix the bone screw 20 inserted into the screw insertion hole 12a, 12b, 12c.

Figure 4:
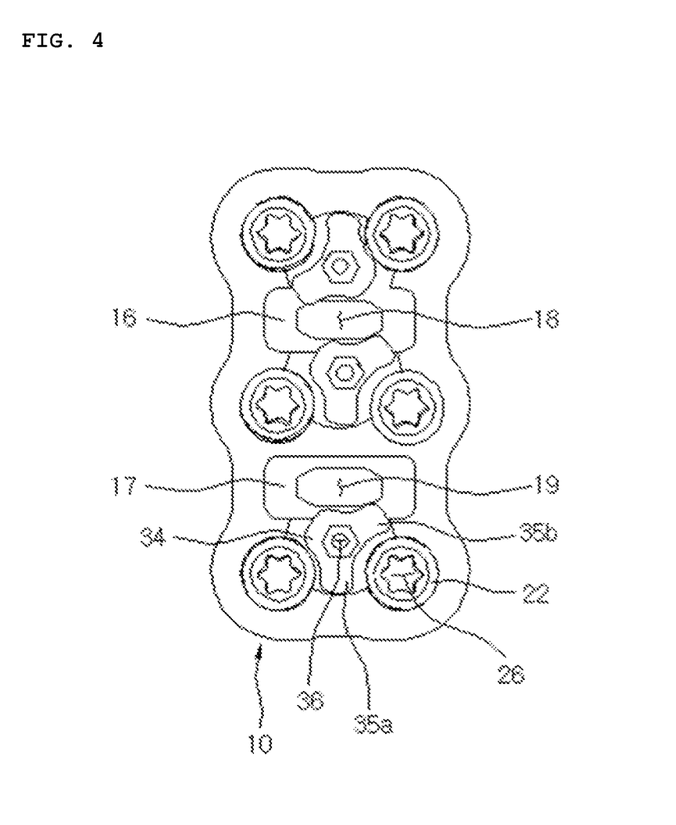
FIG. 4 is a plan view showing the state in which the fixing wing shown in FIG. 3 has rotated 90°.

FIG. 4 shows the state in which the fixing wings 35a and 35b shown in FIG. 3 has rotated 90° on the basis of the central axis of the rotation hole 36. In this state, the fixing wings 35a and 35b do not close the top of the screw insertion hole 12a, 12b, 12c.

Figure 5:
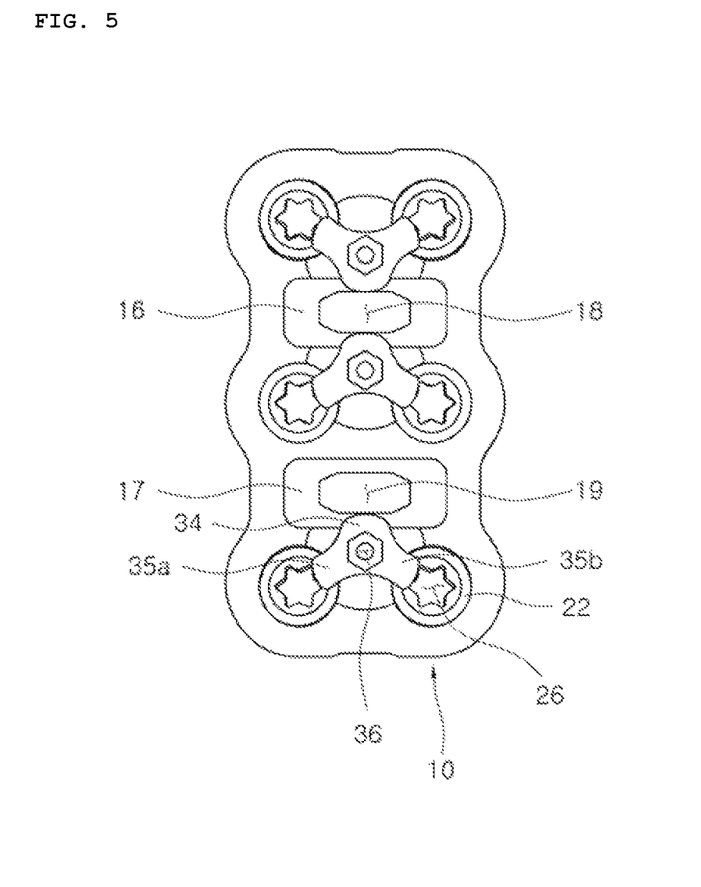
FIG. 5 is a plan view showing the state in which the fixing wing shown in FIG. 3 is located in a rotation area.

FIG. 5 shows the state in which the fixing wings 35a and 35b shown in FIG. 4 have further rotated 90° on the basis of the central axis of the rotation hole 36. In this state, the wing angle of the fixing wings 35a and 35b becomes the same as the closed angle and the wing angle shuts the top of the screw insertion hole 12a, 12b, 12c, thereby preventing the drawing of the bone screw 20 inserted into the screw insertion hole 12a, 12b, 12c. Through such a process, the drawing of the bone screw 20 inserted into the plate 10 can be easily prevented by only the rotation of the locking part 30.

A procedure method using the apparatus 1 for fixing a cervical spine according to an embodiment of the present invention is described below.

First, an operator performs an operation of a surgical procedure matter, such as a cage, on the lesion of a patient who has suffered a cervical spine fracture. The operator covers the lesion with the plate 10 while checking an accurate location of the lesion through the vision holes 18 and 19.

When the plate 10 comes into contact with the accurate location of the lesion, the operator rotates the locking part 30 formed in the plate 10 in the state in which it has opened the top of the screw insertion hole 12a, 12b, 12c and inserts the bone screw 20 into the screw insertion hole 12a, 12b, 12c.

Thereafter, the operator couples a clamping device (not shown) to the clamping device hole 26 of the inserted bone screw 20 and performs screw coupling to a fractured cervical spine by rotating the bone screw 20 in one direction.

When all the bone screws 20 are screwed through the screw insertion holes 12a, 12b and 12c formed in the plate 10, the operator inserts a rotation tool, such as a driver (not shown), into the rotation hole 36 formed in the locking part 30 and rotates the rotation tool. When the locking parts 30 close all of the tops of the screw insertion holes 12a, 12b and 12c, the operator stops the rotation.

In accordance with an embodiment of the present invention, the drawing of the bone screw can be prevented by shutting the top of the plate through a simple rotation manipulation of the locking part.

Furthermore, in accordance with an embodiment of the present invention, a phenomenon in which the locking part is caught due to the activities of a patient can be prevented because the locking part is seated in the stepped part formed in the plate.

Although the present invention has been described in connection with the limited embodiments and drawings, the present invention is not limited to them. A person having ordinary skill in the art to which the present invention pertains may change or modify the present invention in various ways within the technological spirit of the present invention and the equivalent range of the claims to be described below.

We claim:

1. An apparatus for fixing a cervical spine, comprising:
   a plate in which a plurality of screw insertion holes is formed;
   bone screws inserted into the screw insertion holes and configured to be screwed onto a bone fragment through rotation; and
   a locking part rotatably coupled to the plate to open or close a top of a screw insertion hole,
   wherein a stepped part of a specific depth is formed on top of the plate,
   the stepped part comprises a rotation area in which the locking part is capable of rotating,
   a central area to guide the rotation of the locking part is provided between a plurality of the rotation areas provided in the stepped part,
   a locking part insertion hole is formed in the rotation area so that the locking part is inserted into the locking part insertion hole, and
   a vision hole that penetrates the plate is formed in the central area so as to check a procedure state,
   wherein the locking part includes a plurality of fixing wings protruded from the locking part and disposed in a non-radial type with respect to a center of the locking part, and
   wherein a fixing wing is overlapped with the bone screw by rotation to fix the bone screw, the locking part is provided so as not to overlap with the vision hole.

2. The apparatus of claim 1, wherein the locking part comprises:
   a vertical part inserted into the locking part insertion hole;
   a horizontal part integrally coupled to the vertical part and coming into surface contact with the rotation area; and
   the plurality of fixing wings formed in the horizontal part and simultaneously opening or shutting tops of two screw insertion holes adjacent to the rotation area.

3. The apparatus of claim 2, wherein an angle between the plurality of fixing wings is 120°.

4. The apparatus of claim 2, wherein:
   a fixing wing located in the rotation area shuts the top of the screw insertion hole, and
   a fixing wing located in the central area opens the top of the screw insertion hole.

5. The apparatus of claim 2, wherein a molding head part is formed at one end of the vertical part in order to prevent the locking part from being drawn after the locking part is inserted into the locking part insertion hole.

6. The apparatus of claim 2, wherein a rotation hole is formed in the horizontal part so that the rotation hole is coupled to a rotation tool and rotates the locking part.

* * * * *